(12) United States Patent
Kusch et al.

(10) Patent No.: US 7,753,587 B2
(45) Date of Patent: Jul. 13, 2010

(54) PATIENT TABLE FOR A RADIATION THERAPY SYSTEM OR A RADIATION DIAGNOSIS SYSTEM

(75) Inventors: Jochen Kusch, Wachtberg (DE); Jürgen Plannerer, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/662,738

(22) PCT Filed: Sep. 16, 2005

(86) PCT No.: PCT/EP2005/054629

§ 371 (c)(1),
(2), (4) Date: Mar. 13, 2007

(87) PCT Pub. No.: WO2006/032637

PCT Pub. Date: Mar. 30, 2006

(65) Prior Publication Data

US 2008/0013693 A1    Jan. 17, 2008

Related U.S. Application Data

(60) Provisional application No. 60/612,232, filed on Sep. 22, 2004.

(51) Int. Cl.
*A61B 6/04* (2006.01)

(52) U.S. Cl. ..................................... 378/209

(58) Field of Classification Search .................. 378/209
See application file for complete search history.

(56) References Cited

U.S. PATENT DOCUMENTS 3,449,570 A * 6/1969 Kok ........................... 378/209
3,897,345 A    7/1975 Foster
5,054,049 A    10/1991 Manabe

FOREIGN PATENT DOCUMENTS

| DE | 10 39 192 | 9/1958 |
| JP | 2-246936 | 5/1983 |
| JP | 58-98902 | 2/1990 |

OTHER PUBLICATIONS

International Written Opinion for PCT/EP2005/054629 (and translation).
Japanese Office Action dated Oct. 21, 2009 for Japanese Patent Application No. 2007-532887.

\* cited by examiner

*Primary Examiner*—Hoon Song
*Assistant Examiner*—Mona M Sanei
(74) *Attorney, Agent, or Firm*—Brinks, Hofer, Gilson & Lione

(57) ABSTRACT

A patient table for a medical radiation therapy system or radiation diagnosis system is provided. The patient table includes a flat bearing surface and a surface-specific radiation absorption that is measured per radiated surface unit of the bearing surface. The perpendicular incidence radiation reduces along a transversal direction from a central longitudinal plane of the patient table to both of the lateral edges.

18 Claims, 2 Drawing Sheets

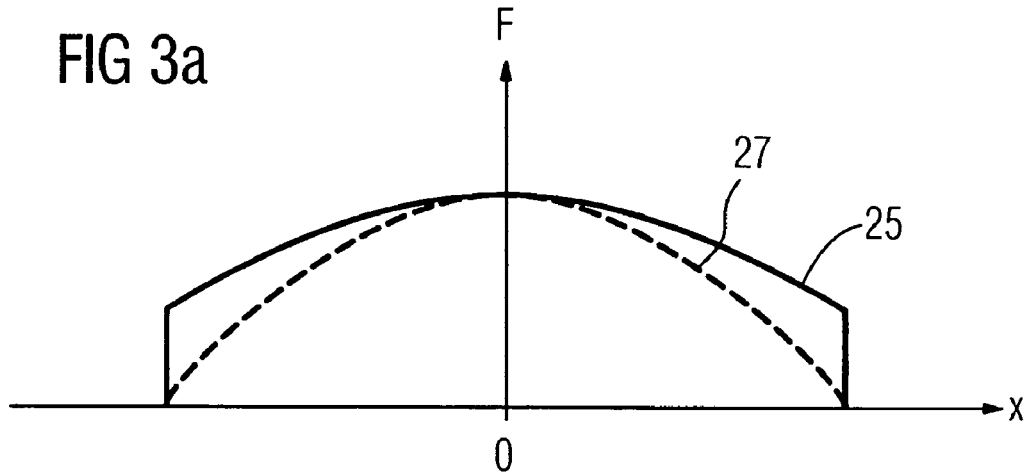
FIG 3a
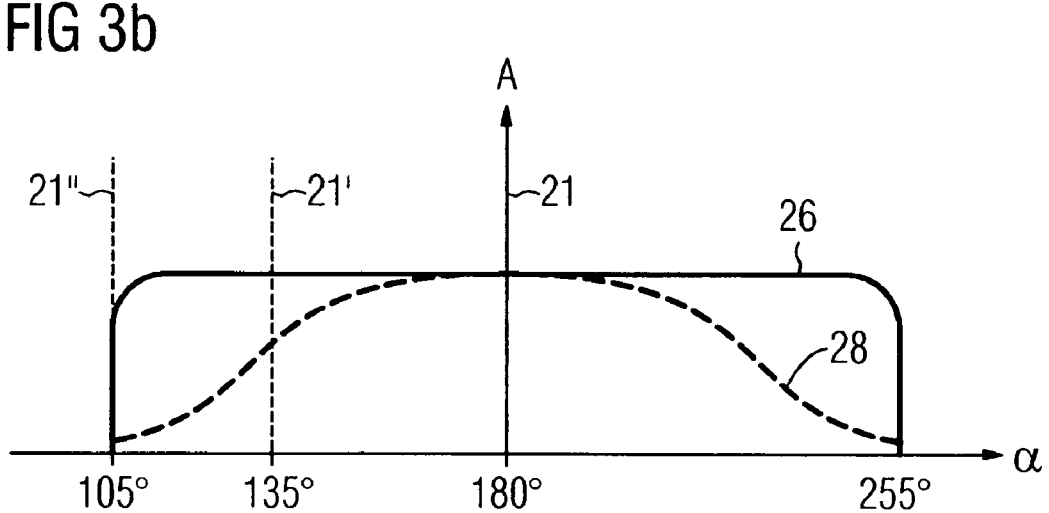
FIG 3b
FIG 3

PATIENT TABLE FOR A RADIATION THERAPY SYSTEM OR A RADIATION DIAGNOSIS SYSTEM

The present patent document is a 35 U.S.C. §371 nationalization application of PCT Application Serial Number PCT/EP2005/054629 filed Sep. 16, 2005, designating the United States, which is hereby incorporated by reference, which claims the benefit pursuant to 35 U.S.C. §119(e) of U.S. provisional application 60/612,232, filed Sep. 22, 2004, which is hereby incorporated by reference.

BACKGROUND

The present embodiments relate to a patient table for a medical radiation therapy system or a radiation diagnosis system. The term radiation includes both particle radiation (i.e. electrons, protons) and high-energy electromagnetic radiation (i.e. x-rays, gamma rays).

A conventional radiation therapy system or radiation diagnosis system includes a patient table that always exhibits an absorption behavior. The radiation intensity is weakened when passing through the patient table because of the absorption behavior. This weakening is generally unwanted and can, particularly in the case of an imaging diagnosis system, have an adverse effect on the image quality. To reduce the radiation absorption, patient tables are formed from a support jacket made of a carbon fiber material. The carbon fiber material encloses a cavity. The cavity is filled with a weakly absorbent foam material.

In a conventional patient table, the strength of the radiation absorption is also dependent on the angle of incidence, at which the radiation hits the bearing surface of the patient table. With a radiation diagnosis method, in particular a tomography method, the angle dependency of the absorption behavior can result in the examination result being impaired. With a radiation therapy method, the angle-dependent radiation absorption of the patient table results in an unwanted local movement of the absorption density in the body tissue of the patient to be treated. In particular, the radiated body region generally moves toward the body surface, thereby resulting in skin irritations or burns.

SUMMARY

The present embodiments may obviate one or more of the limitations or drawbacks inherent in the related art. For example, in one embodiment, a patient table includes an essentially flat bearing surface, which has a surface-specific radiation absorption measured per radiated surface unit of the bearing surface with perpendicular incidence radiation. The perpendicular incidence radiation reduces along a transversal direction from a central longitudinal plane of the patient table toward both of the lateral edges.

The patient table includes an essentially flat bearing surface. The surface-specific radiation absorption of the bearing surface to be assigned as a parameter to the patient table reduces starting from a central longitudinal plane of the patient table to both of the lateral edges.

The radiation absorption is a surface-specific radiation absorption, which is measured in a locally dependent manner per surface unit of the bearing surface, with a perpendicular incidence radiation on the bearing surface.

Conventionally, the radiation absorption of the patient table is greater the more inclined the angle at which the radiation arrives at the patient table, for example, the greater the angle of incidence formed between the radiation path and the solder on the bearing surface. In the case of a radiation therapy system or radiation diagnosis system, the radiation path for all angles of incidence is frequently aligned to an isocentric axis. The isocentric axis is arranged in a region where the longitudinal axis of the body of a patient mounted on the patient table is typically located during a therapy and/or examination. The position of the isocentric axis with respect to the patient table is herewith determined. The isocentric axis generally runs within the central longitudinal plane of the patient table and is mounted in front of the bearing surface at a predetermined, constant distance.

The isocentric axis forms a geometric center of rotation in the transverse section through the patient table. The radiation path rotates about the isocentric axis with respect to the patient table in the event of a change in the angle of incidence. Once the isocentric axis is arranged in front of the bearing surface, the transmission section of the radiation path through the patient table deviates more intensively from the central longitudinal plane of the patient table, the greater the angle of incidence chosen. In practice, the radiation passes through a laterally offset region of the patient table, the more inclined its alignment is with respect to the bearing surface.

When the surface-specific radiation absorption reduces toward the lateral edges, the increase in the radiation absorption that usually occurs with a patient table is completely or partially compensated when using an increasingly inclined irradiation.

In one embodiment, the surface-specific radiation absorption is a continual function of the distance from the central longitudinal plane of the patient table. A constant reduction in the surface-specific radiation absorption is continuous. However, a variation in the surface-specific radiation absorption is also continuous. The variation takes place at an increasing distance from the central longitudinal plane in several discrete steps. The patient table is designed such that the surface-specific radiation absorption reduces symmetrically with respect to the central longitudinal plane.

An angle-dependent radiation absorption variable is used to characterize the absorption behavior of the patient table. The angle-dependent radiation absorption is the radiation absorption which is measured as a function of the angle of incidence for the radiation, which transmit the patient table at a different angle of incidence and are aligned in each instance to a common isocenter, with this isocenter, i.e. the sectional point of an isocentric axis with a cross-sectional plane of the patient table, being arranged within the central longitudinal plane at a predetermined distance above the bearing surface. The distance of the isocenter from the bearing surface here preferably amounts to between 10 and 20 cm.

The isocentric axis to be assigned to the patient table coincides with the isocentric axis of a gantry. The gantry retains a radiation generator of the radiation therapy system and/or an emitter detector unit of the radiation diagnosis system in a rotatable fashion.

With a conventional patient table, the angle-dependent radiation absorption increases the more the angle of incidence deviates from the value 180° (according to the perpendicular incidence radiation on the bearing surface). Alternatively, in one embodiment, the patient table is designed such that the angle-dependent radiation absorption is constant, for example, includes the same value, for different angles of incidence.

In one embodiment, the patient table is designed such that the angle-dependent radiation absorption includes an approximately bell-shaped dependency on the angle of incidence. The maximum lies at an angle of incidence of 180° (according to perpendicular incidence radiation). The radiation absorption produced by the patient table represents a "soft," for example, a varied, angle of incidence, only gradually increasing and/or decreasing interference.

In one embodiment, the patient table includes a support jacket made of a fiber composite material, in particular a carbon fiber composite material. The cavity is enclosed by the support jacket and is filled with a foam core. The patient table has high mechanical stability and low radiation absorption.

The patient table is designed such that its table strength to be measured perpendicular to the bearing surface reduces starting from the central longitudinal plane toward both of the lateral edges. In the case of vertical incidence radiation, the transmission path is also successively reduced toward the table sides.

In one embodiment, the patient table includes a triangular or trapezoid cross-sectional form. In an alternative embodiment, the patient table includes a table underside that is convexly curved in its cross-section. The patient table includes a cross-sectional surface in the form of a circular segment, or a symmetrical parallel segment or other suitable sized segment.

The patient table is designed to influence the surface-specific radiation absorption such that the (volume specific) absorption coefficient of the support jacket and/or of the foam core is varied as a function of the distance from the central longitudinal plane.

A larger number of parallel fiber layers are arranged in the central region centered about the central longitudinal plane. The fiber layers locally increase the absorption coefficient in a central region centered about the central longitudinal plane. The parallel fiber layers are disposed one above the other in the bordering side regions of the patient table.

In one embodiment, the foam core has a locally-dependent different absorption coefficient. The foam core includes a locally differentiated weakly absorbent or comparatively strongly absorbent filling material.

BRIEF DESCRIPTION OF THE DRAWINGS

FIG. 3a is a schematic diagram of one embodiment of the patient table of the surface-specific radiation absorption as a function of the distance from the central longitudinal plane of the patient table, and FIG. 3b is a schematic diagram of one embodiment of the patient table of the angle-dependent radiation absorption as a function of the angle of incidence.

DETAILED DESCRIPTION

Figure 1:
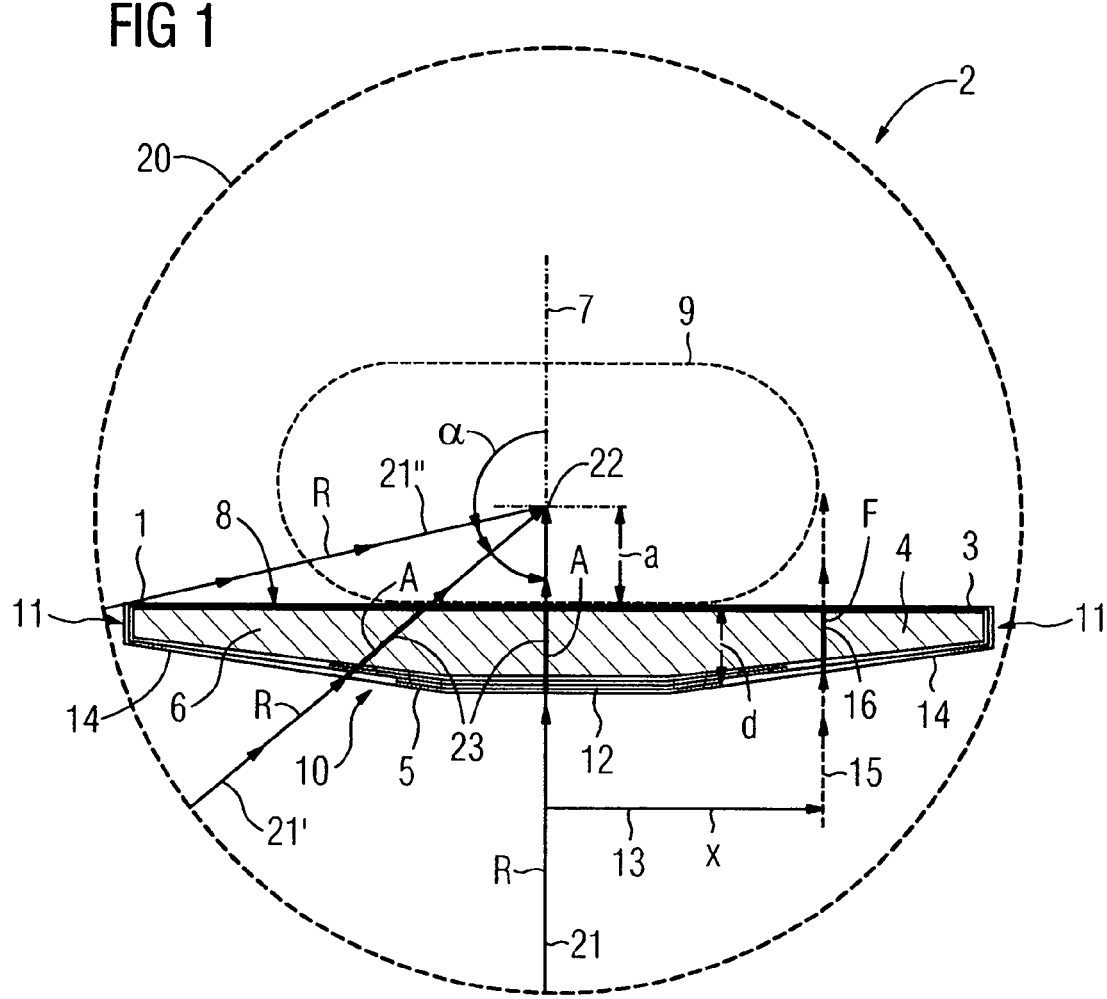
FIG. 1 is a schematic cross-sectional view of one embodiment of a patient table in a radiation therapy system or radiation diagnosis system.

Parts and variables which correspond to each other are provided with the same reference characters in all the figures.

FIG. 1 shows a schematic cross-sectional view of a patient table 1 of a radiation therapy system or radiation diagnosis system (subsequently abbreviated to system 2). System 2 is a radiation system or a computed tomography device equipped for instance with a linear accelerator as a radiation generator.

The patient table 1 includes a support jacket 3. The support jacket 3 forms the surface of the patient table 1 and surrounds a cavity 4 on all sides. The support jacket 3 includes a carbon fiber composite material. The carbon fiber composite material is formed from several fiber layers 5 that are overlaid in layers one on top of the other and are embedded in a polymer material. The cavity 4 is enclosed by the support jacket 3 and is filled with a foam core 6, in particular made of Rohacell.

The patient table 1 has a flat cross-sectional form arranged in an assembly position horizontally in the space. The cross-sectional form in the table longitudinal direction (i.e. perpendicular to the reference plane in FIG. 1) is constant and symmetrical with respect to a central longitudinal plane 7 aligned perpendicularly in the room. The top of the patient table 1 includes a flat bearing surface 8. A patient 9 is mounted on the flat bearing surface 8 for the purpose of a therapy and/or examination. The surface of the patient table 1 pointing downwards in the assembly position and opposing the bearing surface 8 is a base surface 10. The cross-sectional form of the patient table 1 includes a lateral edge 11 on both edges of the bearing surface 8.

In one embodiment, as shown in FIG. 1, the base surface 10 is in a central region 12 centered about the central longitudinal plane 7. The base surface 10 is parallel to the bearing surface 8. A lateral region 14 connects to both sides of the central region 12, in a transversal direction 13. Both lateral regions 14 are curved upwards compared with the central region 12, for example, toward the bearing surface 8. The patient table 1 has a trapezoid-like cross-sectional form. The table strength d to be measured perpendicular to the bearing surface 8 continually reduces starting from the central longitudinal plane 7 toward each lateral edge 11.

A surface-specific radiation absorption F variable is used to measure the absorption characteristics of the patient table 1. The surface-specific radiation absorption F is the radiation absorption that is measured at a predetermined point of the bearing surface 8, with perpendicular incidence radiation 15 on the bearing surface 8, per surface unit of the bearing surface 8.

The surface-specific radiation absorption F is proportional to the transmission section 16, for example, the distance covered by a beam oriented perpendicular to the bearing surface 8 within the patient table 1, and the absorption coefficient of the table material determined by way of the transmission path 16. The value of the surface-specific radiation absorption F is continually reduced by the varying table strength d at an increased (measured in the transversal direction 13) distance x from the central longitudinal plane 7. In one embodiment, the absorption coefficient of the support jacket 3 also reduces with increasing distance x. Additional fiber layers 5 are included in the central region 12 of the base-side support jacket 3. The fiber layers 5 increase the local absorption coefficient. The additional fiber layers 5 have different transverse dilation. The number of parallel fiber layers 5 continually reduces from the central longitudinal plane 7 to both of the lateral edges 11.

To carry out a therapy and/or examination, the patient table 1 can be inserted into a gantry 20 of the system 2. The patient 9 is mounted on the patient table 1. The gantry 20 includes an annularly designed support frame. An emitter and/or an emitter detector unit is suspended in rotatable fashion on the support frame. The emitter detector unit is used in the case of a radiation diagnosis system. The gantry 20 includes a circular opening, shown in FIG. 1 by a dashed circle.

The emitter is attached to the gantry 20 such that the radiation path 21, 21', 21" of the generated radiation R for all orientations is always aligned to an isocentric axis 22 arranged in the circular central point of the gantry 20. The patient table 1 is aligned with respect to the isocentric axis 22 such that the isocentric axis 22 crosses the central longitudinal plane 7 at a predetermined distance a above the bearing surface 8. The distance a is preferably 10-20 cm. The isocentric axis 22 approximately coincides with the longitudinal axis of the body of the patient 9 mounted on the bearing surface 8 during the therapy and/or examination.

An angle of incidence α is defined by orienting the emitter with respect to the bearing surface 8. According to FIG. 1, a beam directed perpendicularly from above onto the bearing surface 8 has an angle of incidence of α=0°. A radiation path 21 (shown in FIG. 1) directed perpendicularly from below onto the bearing surface 8 has an angle of incidence of α=180°. As shown in FIG. 1, two exemplary radiation paths 21' and 21", correspond to angles of incidence of approximately α=130° and/or α=105°. The radiation path 21" corresponds to the borderline case where the radiation R still covers the patient table 1.

The radiation R passes through the patient table 1 along a generally inclined transmission path 23. The position and length of the radiation R depends on the selected angle of incidence α.

The net absorption produced during the irradiation (subsequently referred to as angle-dependent radiation absorption A) is a function of the angle of incidence α.

Figure 2:
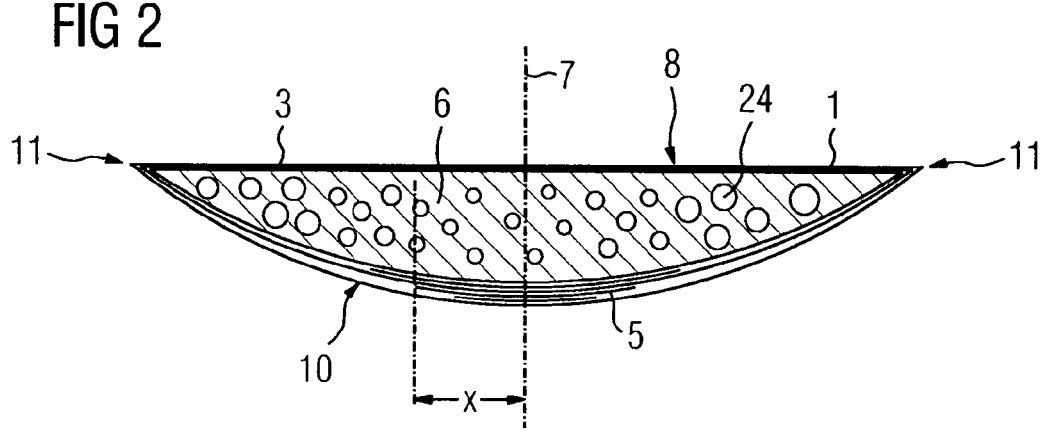
FIG. 2 is an alternative embodiment of the patient table shown in FIG. 1.

In one embodiment, as shown in FIG. 2, the base surface 10 is convexly curved. The patient table 1 includes a circularly segmented cross-sectional profile. The absorption coefficient of the foam core 6 is modified as a function of the distance x in accordance with FIG. 2 in order to modify the surface-specific radiation absorption F. The surface-specific radiation absorption F is modified by providing the foam core 6 with minimally absorbent filling material 24 of different sizes and of different densities. Air-filled polymer globules or other suitable material is used as filling material 24.

The absorption behavior of the patient table 1 shown in FIGS. 1 and 2 is subsequently schematically illustrated in FIG. 3 on the basis of two diagrams. The exemplary embodiment of the patient table 1 is shown using the solid line curves 25 and 26. The exemplary embodiment of the patient table 1 shown in FIG. 2 is shown using the dashed line curves 27 and 28.

In a diagram shown in FIG. 3a, the surface-specific radiation absorption F is shown as a function of the distance x. For both variants of the patient table 1, the surface-specific radiation absorption F reduces at an increasing distance x in symmetry to the central longitudinal plane 7 (i.e. x=0).

As shown in FIG. 3b, the course of the angle-dependent radiation absorption A is shown as a function of the angle of incidence α, as is realized by the embodiment of the patient table 1 according to FIG. 1 or FIG. 2. As shown in FIG. 3b, the embodiment of the patient table 1 according to FIG. 1 is designed by suitably varying the table thickness d and the number of parallel fiber layers 5 at an increasing distance x such that the angle-dependent radiation absorption A is essentially independent of the angle of incidence α (curve 26). In the exemplary embodiment according to FIG. 2, the angle-dependent radiation absorption A includes a bell-shaped dependency centered about an angle of incidence of α=180° (curve 28). The angle-dependent radiation absorption A is maximum with an angle of incidence of α=180° and reduces for larger or smaller angles of incidence α in an approximately symmetrical form.

Various embodiments described herein can be used alone or in combination with one another. The forgoing detailed description has described only a few of the many possible implementations of the present invention. For this reason, this detailed description is intended be way of illustration, and not by way of limitation. It is only the following claims, including all equivalents that are intended to define the scope of this invention.

The invention claimed is:

1. A patient table for a medical radiation therapy system or radiation diagnosis system, comprising:
    a bearing surface having a top surface and a base surface, the bearing surface having a surface radiation absorption, the surface radiation absorption being measured per radiated surface unit of the bearing surface, and
    a support jacket surrounding a cavity, where a cavity thickness of the cavity is continuously reduced from a central longitudinal plane toward first and second lateral edges of the bearing surface,
    wherein radiation that is perpendicularly incident on the bearing surface reduces along a transversal direction from the central longitudinal plane of the bearing surface toward the first and second lateral edges of the bearing surface,
    wherein an angle-dependent radiation absorption of the bearing surface is a function of an angle of incidence along a radiation path that is aligned to a central isocenter, the central isocenter being disposed at a distance above the bearing surface, and
    wherein the top surface has a uniform surface radiation absorption from the first lateral edge to the second lateral edge.

2. The patient table as claimed in claim 1, wherein the surface radiation absorption is continually reduced.

3. The patient table as claimed in claim 2, wherein the surface radiation absorption is symmetrically reduced with respect to the central longitudinal plane.

4. The patient table as claimed in claim 2, wherein the surface radiation absorption is constantly reduced.

5. The patient table as claimed in claim 1, wherein a table strength is reduced from the central longitudinal plane toward the lateral edges.

6. The patient table as claimed in claim 5, wherein a cross-section of the base surface is convexly curved in cross-section from one end of the top surface to an opposite end of the top surface.

7. The patient table as claimed in claim 1, wherein the support jacket is made of a fiber composite material and the cavity is filled with a foam core.

8. The patient table as claimed in claim 7, wherein the support jacket and the foam core each have an absorption coefficient, the absorption coefficient of the support jacket and/or the absorption coefficient of the foam core being reduced from the central longitudinal plane toward the lateral edges.

9. The patient table as claimed in claim 8, wherein the support jacket is disposed in a central region that is centered about the central longitudinal plane, the central region including a larger number of parallel fiber layers than in a bordering lateral region.

10. The patient table as claimed in claim 9, wherein the absorption coefficient of the foam core is modified by the inclusion of filling material as a function of a distance from the central longitudinal axis.

11. The patient table as claimed in claim 7, wherein the support jacket includes a carbon fiber composite material.

12. The patient table as claimed in claim 1, wherein the bearing surface is essentially flat.

13. The patient table as claimed in claim 1, wherein the top surface is not curved.

14. The patient table as claimed in claim 1, wherein a cross-section of the top surface has a uniform thickness in cross-section from the first lateral edge to the second lateral edge.

15. A radiation therapy system comprising:
a patient table that includes:
a bearing surface having a surface radiation absorption, the surface radiation absorption being measured per radiated surface unit of the bearing surface, and
a support jacket surrounding a cavity, where a cavity thickness of the cavity is continuously reduced from a central longitudinal plane toward first and second lateral edges of the bearing surface,
wherein perpendicular incidence radiation is reduced along a transversal direction from a central longitudinal plane of the patient table toward the first and second lateral edges of the bearing surface, and
wherein an angle-dependent radiation absorption of the bearing surface is a function of an angle of incidence along a radiation path that is aligned to a central isocenter, the central isocenter being disposed at a distance above the bearing surface.

16. The radiation therapy system as claimed in claim 15, comprising a gantry that rotatably supports an emitter.

17. A radiation diagnosis system comprising:
a patient table that includes:
a bearing surface having a surface radiation absorption, the surface radiation absorption being measured per radiated surface unit of the bearing surface, and
a support jacket surrounding a cavity, where a cavity thickness of the cavity is continuously reduced from a central longitudinal plane toward first and second lateral edges of the bearing surface,
wherein perpendicular incidence radiation is reduced along a transversal direction from a central longitudinal plane of the patient table toward the first and second lateral edges of the bearing surface, and
wherein an angle-dependent radiation absorption of the bearing surface is a function of an angle of incidence along a radiation path that is aligned to a central isocenter, the central isocenter being disposed at a distance above the bearing surface.

18. The radiation diagnosis system as claimed in claim 17, comprising a gantry that rotatably supports an emitter and/or an emitter detector unit.

* * * * *